(12) United States Patent
Patel et al.

(10) Patent No.: US 12,406,768 B2
(45) Date of Patent: Sep. 2, 2025

(54) SYSTEM AND METHOD FOR COLLECTION AND MANAGEMENT OF DATA FROM MANAGED AND UNMANAGED DEVICES

(71) Applicant: Dell Products L.P., Round Rock, TX (US)

(72) Inventors: Dharmesh M. Patel, Round Rock, TX (US); Prem Pradeep Motgi, Austin, TX (US); Manpreet Singh Sokhi, Santa Clara, CA (US)

(73) Assignee: Dell Products L.P., Round Rock, TX (US)

( * ) Notice: Subject to any disclaimer, the term of this patent is extended or adjusted under 35 U.S.C. 154(b) by 260 days.

(21) Appl. No.: 18/190,481

(22) Filed: Mar. 27, 2023

(65) Prior Publication Data

US 2024/0331857 A1    Oct. 3, 2024

(51) Int. Cl.
  *G16H 40/67*    (2018.01)
  *G16H 10/60*    (2018.01)
  *G16H 40/40*    (2018.01)
  *G16H 50/70*    (2018.01)

(52) U.S. Cl.
  CPC ............. *G16H 40/67* (2018.01); *G16H 10/60* (2018.01); *G16H 40/40* (2018.01); *G16H 50/70* (2018.01)

(58) Field of Classification Search
  CPC ........ G16H 40/67; G16H 10/60; G16H 40/40; G16H 50/70
  See application file for complete search history.

(56) References Cited

U.S. PATENT DOCUMENTS

| | | |
|---|---|---|
| 6,606,620 B1 | 8/2003 | Sundaresan |
| 8,117,235 B1 | 2/2012 | Barta |
| 8,255,948 B1 | 8/2012 | Black et al. |
| 9,361,428 B2 | 6/2016 | Bessette |
| 9,571,890 B1 | 2/2017 | Diamondstein |
| 10,073,948 B2 | 9/2018 | Cohen et al. |

(Continued)

FOREIGN PATENT DOCUMENTS

| | | |
|---|---|---|
| CN | 202058147 U | 11/2011 |
| CN | 115292285 A | 11/2022 |

(Continued)

OTHER PUBLICATIONS

Balaskas, Georgios, et al., "An end-to-end system for transcription, translation, and summarization to support the co-creation process. A Health CASCADE Study", ACM PETRA '23, published Aug. 10, 2023, pp. 625-631. (Year: 2023) (7 Pages).

(Continued)

*Primary Examiner* — Peter H Choi
*Assistant Examiner* — Aaisha Abdullah
(74) *Attorney, Agent, or Firm* — WOMBLE BOND DICKINSON (US) LLP (57) ABSTRACT

Methods and systems for managing collection of diagnostic data are disclosed. To collect diagnostic data, unmanaged devices may be used. The unmanaged devices may be registered with a data management system. During the registration process, procedures for processing diagnostic data from the unmanaged devices may be established. The procedures may be established based on data collection performance of the unmanaged devices. The procedures may reduce the likelihood of use of diagnostic data that is unreliable.

20 Claims, 6 Drawing Sheets

(56) References Cited

U.S. PATENT DOCUMENTS

| | | |
|---|---|---|
| 11,010,392 B1 | 5/2021 | Hirsch et al. |
| 11,094,402 B2 | 8/2021 | Brown et al. |
| 11,217,331 B2 | 1/2022 | Vishnubhatla et al. |
| 11,631,401 B1 | 4/2023 | Nudd |
| 11,763,821 B1 | 9/2023 | McNair |
| 11,849,069 B1 | 12/2023 | Can |
| 12,135,708 B2 | 11/2024 | Chermside |
| 2003/0046401 A1 | 3/2003 | Abbott |
| 2005/0160166 A1 | 7/2005 | Kraenzel |
| 2008/0154961 A1 | 6/2008 | Dougall |
| 2008/0275701 A1 | 11/2008 | Wu et al. |
| 2009/0171692 A1 | 7/2009 | Zilberman et al. |
| 2009/0300170 A1* | 12/2009 | Bhame .................... H04L 45/00 709/224 |
| 2010/0169304 A1 | 7/2010 | Hendricksen et al. |
| 2011/0131174 A1 | 6/2011 | Birch et al. |
| 2012/0265771 A1 | 10/2012 | Suh |
| 2014/0181673 A1 | 6/2014 | Work |
| 2014/0201199 A1 | 7/2014 | Hajaj |
| 2014/0207885 A1 | 7/2014 | Baker et al. |
| 2014/0245398 A1* | 8/2014 | Son ......................... H04W 4/08 726/4 |
| 2014/0288947 A1* | 9/2014 | Simpson ................. G16H 40/67 705/2 |
| 2014/0344288 A1 | 11/2014 | Evans |
| 2015/0067176 A1* | 3/2015 | Dubois ............... H04W 12/086 709/227 |
| 2015/0169574 A1 | 6/2015 | Bau et al. |
| 2015/0199268 A1 | 7/2015 | Davis et al. |
| 2015/0356127 A1 | 12/2015 | Pierre et al. |
| 2016/0006839 A1 | 1/2016 | Sawazaki |
| 2016/0087976 A1* | 3/2016 | Kaplan ............... H04L 63/0823 713/156 |
| 2016/0164813 A1 | 6/2016 | Anderson |
| 2016/0231928 A1 | 8/2016 | Lewis et al. |
| 2016/0232159 A1 | 8/2016 | Parikh |
| 2016/0306812 A1 | 10/2016 | McHenry et al. |
| 2017/0013047 A1 | 1/2017 | Hubbard |
| 2017/0078195 A1* | 3/2017 | Raman .................... H04W 4/70 |
| 2017/0262164 A1 | 9/2017 | Jain |
| 2017/0365101 A1 | 12/2017 | Samec et al. |
| 2018/0068108 A1* | 3/2018 | Fish ....................... G06F 21/316 |
| 2018/0121502 A1 | 5/2018 | Prieur |
| 2018/0189352 A1 | 7/2018 | Ghafourifar |
| 2018/0203612 A1 | 7/2018 | Kats et al. |
| 2019/0012931 A1 | 1/2019 | Candelore |
| 2019/0079855 A1* | 3/2019 | Dewitt ................. G06F 11/3688 |
| 2019/0279744 A1 | 9/2019 | Howley et al. |
| 2019/0297035 A1 | 9/2019 | Fox et al. |
| 2019/0325036 A1 | 10/2019 | Edge |
| 2020/0110882 A1 | 4/2020 | Ripolles Mateu et al. |
| 2020/0226216 A1 | 7/2020 | Marin et al. |
| 2020/0258516 A1 | 8/2020 | Khaleghi |
| 2021/0056131 A1 | 2/2021 | Ackermann et al. |
| 2021/0065203 A1 | 3/2021 | Billigmeier et al. |
| 2021/0256534 A1 | 8/2021 | An |
| 2021/0390196 A1 | 12/2021 | Lavine et al. |
| 2022/0059216 A1* | 2/2022 | Lewis .................. G06Q 50/265 |
| 2022/0078007 A1* | 3/2022 | Reddem ............. H04L 63/0815 |
| 2022/0261152 A1 | 8/2022 | Jude et al. |
| 2022/0293087 A1 | 9/2022 | Kumar |
| 2022/0334719 A1 | 10/2022 | Thrane |
| 2022/0366131 A1 | 11/2022 | Ekron |
| 2023/0061725 A1 | 3/2023 | Khan |
| 2023/0068099 A1 | 3/2023 | Abramenko et al. |
| 2023/0137931 A1 | 5/2023 | Song |
| 2023/0221911 A1 | 7/2023 | Bandameedipalli |
| 2023/0319026 A1* | 10/2023 | Waltermann ........ H04L 63/0823 726/3 |
| 2025/0017547 A1* | 1/2025 | Raveendranath ...... A61B 6/542 |

FOREIGN PATENT DOCUMENTS

| | | |
|---|---|---|
| JP | 4808173 B2 | 11/2011 |
| JP | 2015-106406 A | 6/2015 |
| WO | 2023/220948 A1 | 11/2023 |

OTHER PUBLICATIONS

"FollowMyHealth®," Allscripts Healthcare Solutions Inc, Google Play Store, Web Page <https://play.google.com/store/apps/details?id=com.jardogs.fmhmobile&hl=en_US&gl=US> accesed on Jan. 8, 2023 (4 Pages).

Page, Sebastien, "How to move your Health data from one iPhone to another," iDB, Web Page <https://www.idownloadblog.com/2016/10/13/health-data-importer-makes-moving-your-health-data-from-one-iphone-to-another-a-breeze/> accessed on Oct. 30, 2022 (9 Pages).

"MyChart," Web Page <https://www.mychart.org/> accessed on Oct. 30, 2022 (6 Pages).

Xu, Jie, et al., "Federated learning for healthcare informatics," Journal of Healthcare Informatics Research 5 (2021): 1-19. (19 Pages).

Naz, Sadaf, et al., "A comprehensive review of federated learning for COVID-19 detection," International Journal of Intelligent Systems 37.3 (2022): 2371-2392. (22 Pages).

Prasser, Fabian, et al., "Efficient and effective pruning strategies for health data de-identification," BMC medical informatics and decision making 16.1 (2016): 1-14. (14 Pages).

D. Fedasyuk and I. Lutsyk, "Tools for adaptation of a mobile application to the needs of users with cognitive impairments," 2021 IEEE 16th International Conference on Computer Sciences and Information Technologies (CSIT), LVIV, Ukraine, 2021, pp. 321-324, doi: 10.1109/CSIT52700.2021.9648702. (Year: 2021).

* cited by examiner

SYSTEM AND METHOD FOR COLLECTION AND MANAGEMENT OF DATA FROM MANAGED AND UNMANAGED DEVICES

FIELD

Embodiments disclosed herein relate generally to data collection. More particularly, embodiments disclosed herein relate to systems and methods to manage collection of diagnostic data.

BACKGROUND

Computing devices may provide computer-implemented services. The computer-implemented services may be used by users of the computing devices and/or devices operably connected to the computing devices. The computer-implemented services may be performed with hardware components such as processors, memory modules, storage devices, and communication devices. The operation of these components and the components of other devices may impact the performance of the computer-implemented services.

BRIEF DESCRIPTION OF THE DRAWINGS

Embodiments disclosed herein are illustrated by way of example and not limitation in the figures of the accompanying drawings in which like references indicate similar elements.

DETAILED DESCRIPTION

Various embodiments will be described with reference to details discussed below, and the accompanying drawings will illustrate the various embodiments. The following description and drawings are illustrative and are not to be construed as limiting. Numerous specific details are described to provide a thorough understanding of various embodiments. However, in certain instances, well-known or conventional details are not described in order to provide a concise discussion of embodiments disclosed herein.

Reference in the specification to "one embodiment" or "an embodiment" means that a particular feature, structure, or characteristic described in conjunction with the embodiment can be included in at least one embodiment. The appearances of the phrases "in one embodiment" and "an embodiment" in various places in the specification do not necessarily all refer to the same embodiment.

References to an "operable connection" or "operably connected" means that a particular device is able to communicate with one or more other devices. The devices themselves may be directly connected to one another or may be indirectly connected to one another through any number of intermediary devices, such as in a network topology.

In general, embodiments disclosed herein relate to methods and systems for managing collection of diagnostic data. The diagnostic data may be usable, for example, to diagnose and/or treat persons for various medical conditions.

The diagnostic data may be collected using managed devices and unmanaged devices. Managed devices may include diagnostic equipment managed by a healthcare provider. Unmanaged devices may include personal electronic devices such as cell phones managed by a person.

To collect diagnostic data using the unmanaged devices, the unmanage devices may be registered with a data collection system. The unmanaged devices may be registered by (i) establishing identification, cryptographic, and/or other types of information usable by the data management system to securely collect diagnostic data from the unmanaged devices, and (ii) establishing procedures for processing diagnostic data collected from the unmanaged devices.

The procedures may be established based on the capabilities of the unmanaged devices. The capabilities may be ascertained through a qualification process. The qualification process may include performance of various actions using the unmanaged devices to obtain a data package. The data package may be used to ascertain limits on the performance of data collection hardware of the unmanaged devices. The limits on the performance of the data collection hardware may be used to establish the procedures. The procedures may improve the likelihood that diagnosis made using the collected diagnostic data are not impacted by the limits on the performance of the data collection hardware.

By collecting diagnostic data using both managed and unmanaged devices, a better picture of the actual condition of a person may be established. The improved picture of the condition of the person may improve the likelihood of accurate diagnosis and corresponding treatment.

By both registering the unmanaged devices and qualifying the collected diagnostic data, security and quality for the collected diagnostic data may be managed. By managing both the security and quality of the collected data, diagnosis and treatment established based on the collected diagnostic data may be less likely to be impacted by the manner in which the diagnostic data is collected. Thus, embodiments disclosed herein may address, among others, the technical problem of data collection using unmanaged devices which may not be subject to similar levels of quality control, upkeep, and maintenance applied to managed devices. By implementing both security and quality control mechanisms for collected diagnostic data, more reliable diagnostic data may be collected.

In an embodiment, a method for managing data collection for managed devices and unmanaged devices is disclosed. The method may include obtaining a request to register an unmanaged device of the unmanaged devices for collection of the data; based on the request to register the unmanaged device: identifying data collection hardware of the unmanaged device; providing a capability test to the unmanaged device, the capability test being based on the data collection hardware; obtaining a measurement package from the unmanaged device, the measurement package being responsive to the capability test; qualifying the unmanaged device for collection of at least a portion of diagnostic data based on the measurement package; and registering the unmanaged device for collection of the at least the portion of the diagnostic data.

Registering the unmanaged device may include assigning an identifier to the unmanaged device; providing the identifier to the unmanaged device; and associating the at least the portion of the diagnostic data with the identifier.

The diagnostic data may include data categories, and the at least the portion of the diagnostic data specifies a subset of the data categories.

The method may also include, after the registering of the unmanaged device is complete: obtaining a second measurement package from the unmanaged device; identifying a first portion of measurement data of the second measurement package, the first portion of the measurement data being a member of the subset of the data categories; identifying a second portion of the measurement data of the second measurement package, the second portion of the measurement data not being a member of the subset of the data categories; storing the first portion of the measurement data; and discarding the second portion of the measurement data.

Storing the first portion of the measurement data may include extracting, from the second measurement package, a stamp based at least in part on the identifier; identifying a user associated with the unmanaged device; and adding the first portion of the measurement data to a record associated with the user.

Adding the first portion of the measurement data may include obtaining cryptographic data based on the user and a host of the record; encrypting the first portion of the measurement data using the cryptographic data; and writing the encrypted first portion of the measurement data to storage for the record.

The method may further include identifying software hosted by the unmanaged device. The capability test may also be based on the software hosted by the unmanaged device.

The unmanaged device may be a person electronic device, and the managed device may be diagnostic equipment.

The personal electronic device may be a smart watch, a communication device, or a wearable sensing system.

The managed devices may be members of a healthcare provider information technology system, and the person electronic device may not be a member of the healthcare provider information technology system.

In an embodiment, a non-transitory media is provided. The non-transitory media may include instructions that when executed by a processor cause the computer-implemented method to be performed.

In an embodiment, a data processing system is provided. The data processing system (or a management controller hosted by the data processing system) may include the non-transitory media and a processor, and may perform the computer-implemented method when the computer instructions are executed by the processor.

Figure 1:
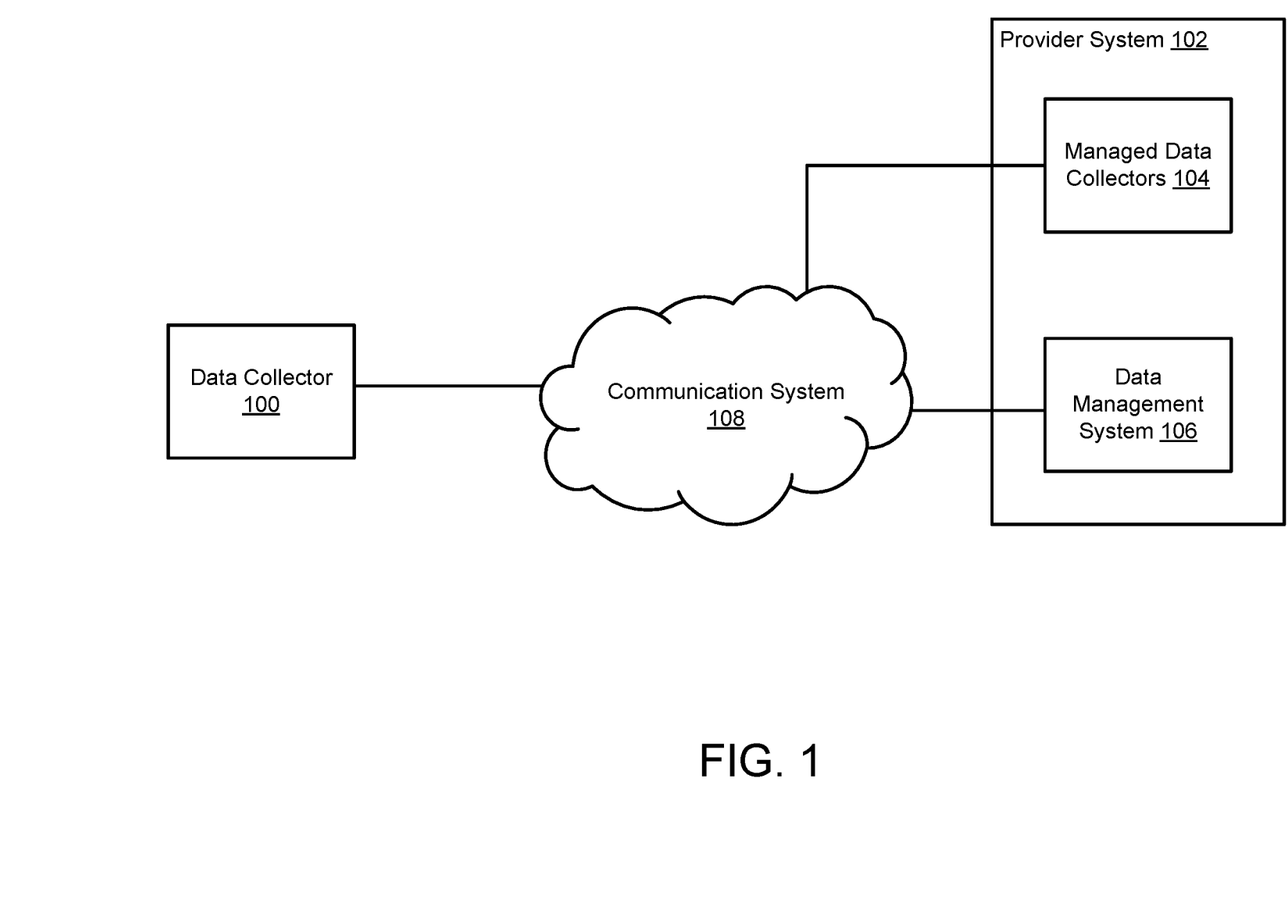
FIG. 1 shows a block diagram illustrating a system in accordance with an embodiment.

Turning to FIG. 1, a block diagram illustrating a system in accordance with an embodiment is shown. The system shown in FIG. 1 may provide computer-implemented services. The computer implemented services may include any type and quantity of computer implemented services. For example, the computer implemented services may include data storage services, instant messaging services, database services, and/or any other type of service that may be implemented with a computing device.

The computer implemented services may be used to provide, for example, healthcare services. For example, the computer implemented services may be utilized by healthcare providers to diagnose patients, store information regarding previously made diagnosis, etc.

To provide the computer-implemented services, the system may include provider system 102. Provider system 102 may facilitate storage and use of information. For example, provider system 102 may aggregate digital medical records, or other types of records, used to provide healthcare and/or other types of services.

Provider system 102 may include managed data collectors 104 and data management system 106. Each of these components is discussed below.

Managed data collectors 104 may facilitate acquisition of diagnostic data regarding patients. Managed data collectors 104 may include any quantity and type of computerized medical equipment. The computerized medical equipment may allow information regarding patients to be obtained, stored, analyzed, etc. For example, a magnetic resonance imaging (MRI) system may be example of a type of computerized medical equipment. The MRI system may utilize sensors to characterize portions of a patient and generate digital records of the characterizations (e.g., records including diagnostic information regarding patients). While described with respect to an example, it will be appreciated that computerized medical equipment may include any type of device through which information regarding a patient may be obtained by sensing characteristics of the patient, samples from a patient, etc.

The information obtained through managed data collectors 104 may be stored for use in data management system 106. Data management system 106 may facilitate storage and use of stored diagnostic information. The stored diagnostic information may be used by medical professionals to diagnose, treat, and/or otherwise manage patient care.

However, the ability of medical providers to provide medical care using the stored diagnostic information may depend on the reliability, fidelity, and other characteristics of the stored diagnostic information. If low reliability diagnostic information is stored in data management system 106, then medical professionals may create care plans that are unlikely to resolve the medical issues impacting patients.

For example, if diagnostic data of low fidelity is stored in data management system 106, a medical professionals may be more likely to miss important details for differential diagnosis between different medical issues that may or may not be impacting patients.

Additionally, the ability of medical providers to provide medical care using the stored diagnostic information may depend on the types and quantity of stored diagnostic information. If insufficient diagnostic information is stored in data management system 106, then medical professionals may be more likely to misdiagnose patients.

In general, embodiments disclosed herein may provide methods, systems, and/or devices for managing collection, storage, and use of diagnostic information (e.g., in aggregate "diagnostic data management services"). The disclosed systems may facilitate increased collection of diagnostic information, improve the reliability of collected diagnostic information, and may improve the security of collected diagnostic information.

To provide diagnostic data management services, the system of FIG. 1 may facilitate collection of diagnostic information from data collector 100. In contrast to managed data collectors 104 which may be professionally managed by medical professionals, data collector 100 may be managed by a patient or other persons that are not medical professionals. For example, data collector 100 may be implemented using, for example, a personal electronic device (e.g., a cell phone, smart phone, a tablet computer, etc.), a personal sensing system (e.g., heart rate monitoring device such as a smart ring or smart watch), or other type of device that may be owned, managed, or used by a patient.

Data collector 100 may include one or more sensors through which information regarding a person may be obtained. The sensors may collect any type and quantity of information regarding the person.

Figure 2A:
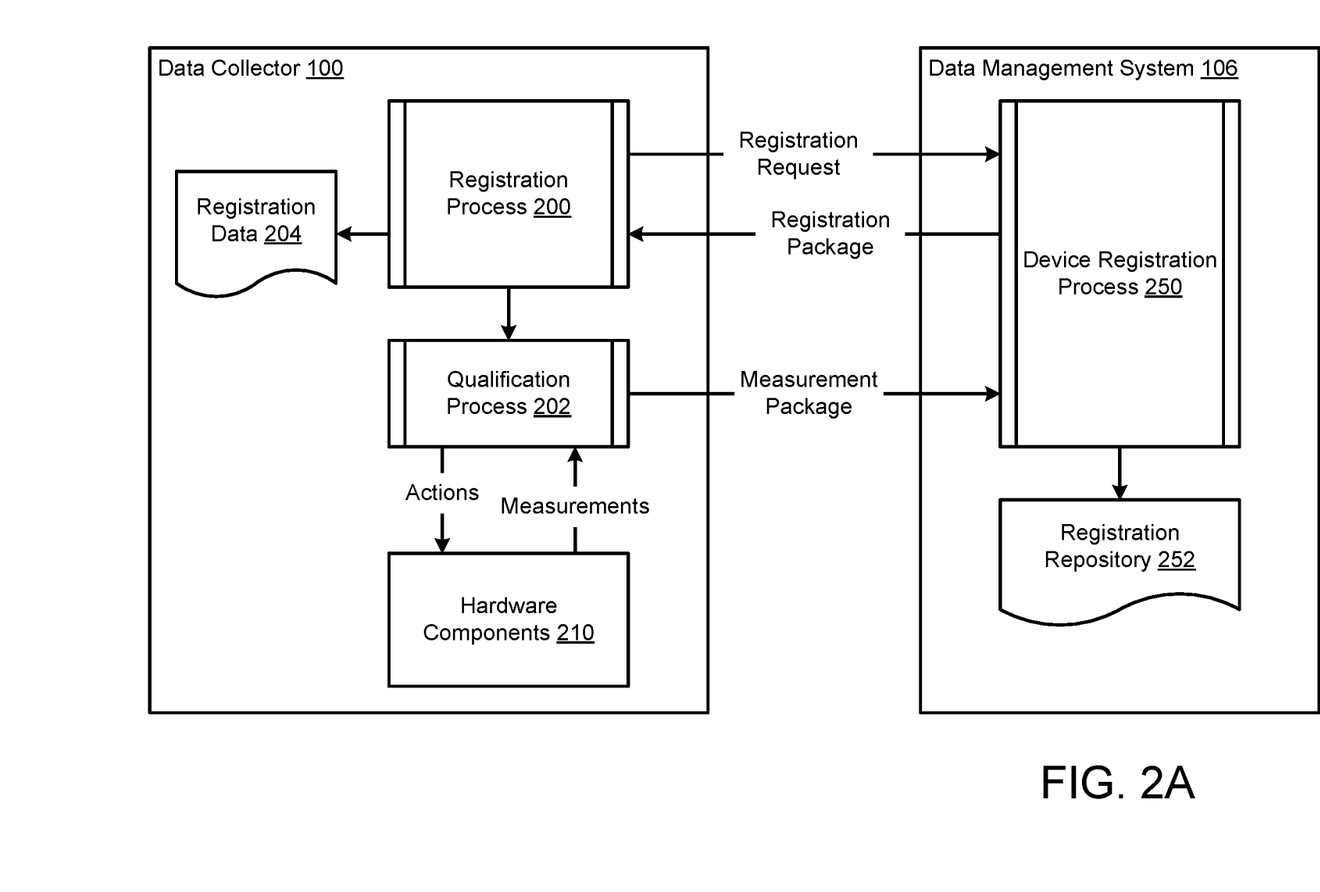
FIGS. 2A-2B show diagrams illustrating data flows in accordance with an embodiment.
Figure 2B:
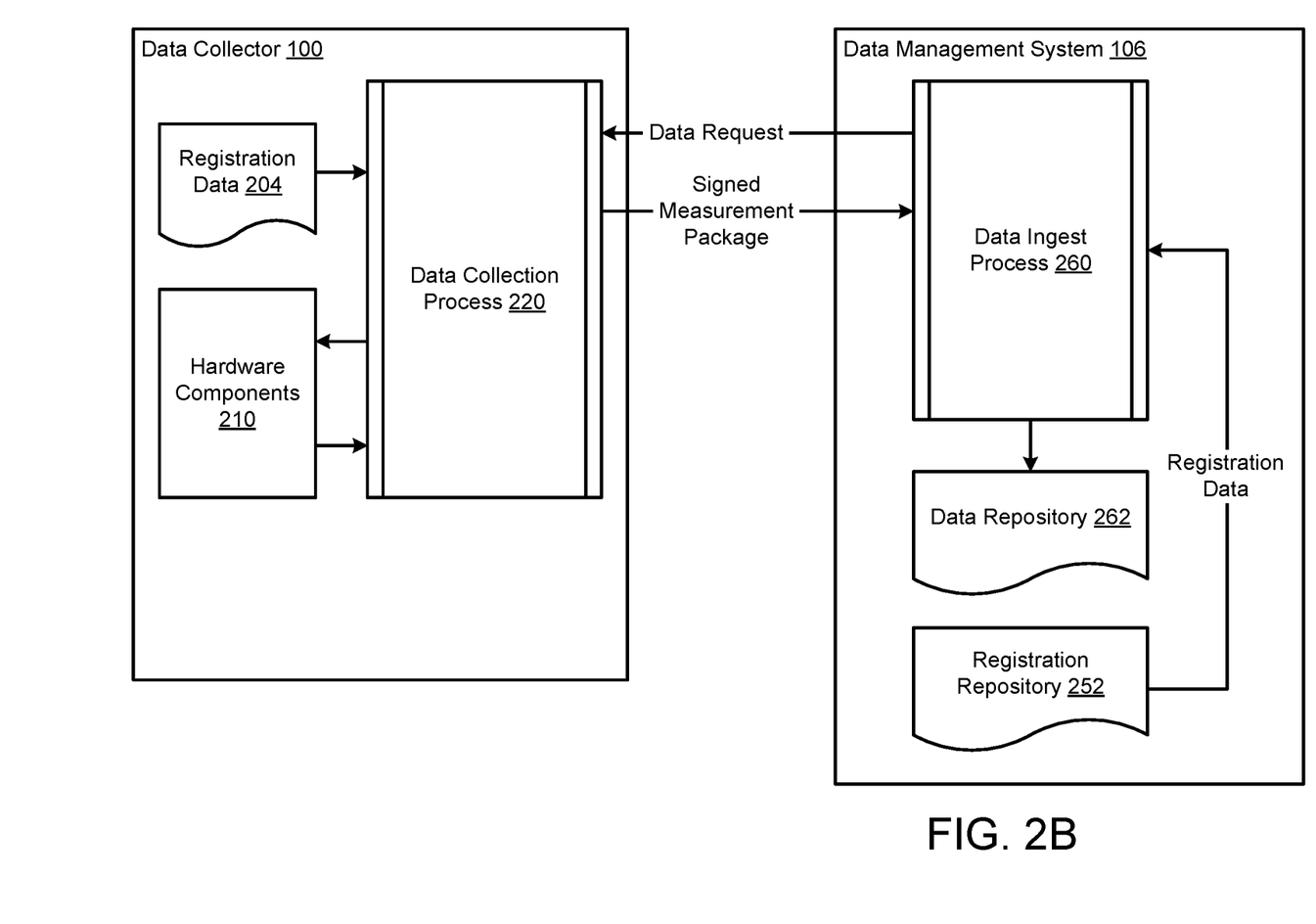

To manage collection of diagnostic data using data collector 100, data management system 106 may (i) register data collector 100, (ii) once registered, qualify data collector 100 with respect to its ability to obtain different type of diagnostic information, (iii) obtain qualified types of diagnostic information obtained from data collector 100, (iv) store the obtained diagnostic data with stamps or other types of metadata usable to characterize the quality of the diagnostic data, and (v) provide access to the diagnostic information and/or information based on the diagnostic information to persons (e.g., medical providers part of provider system 102) and/or other devices (e.g., part of provider system 102). Refer to FIG. 2A for additional details regarding registration of data collector 100. Refer to FIG. 2B for additional details regarding obtaining diagnostic information using data collector 100.

Figure 3A:
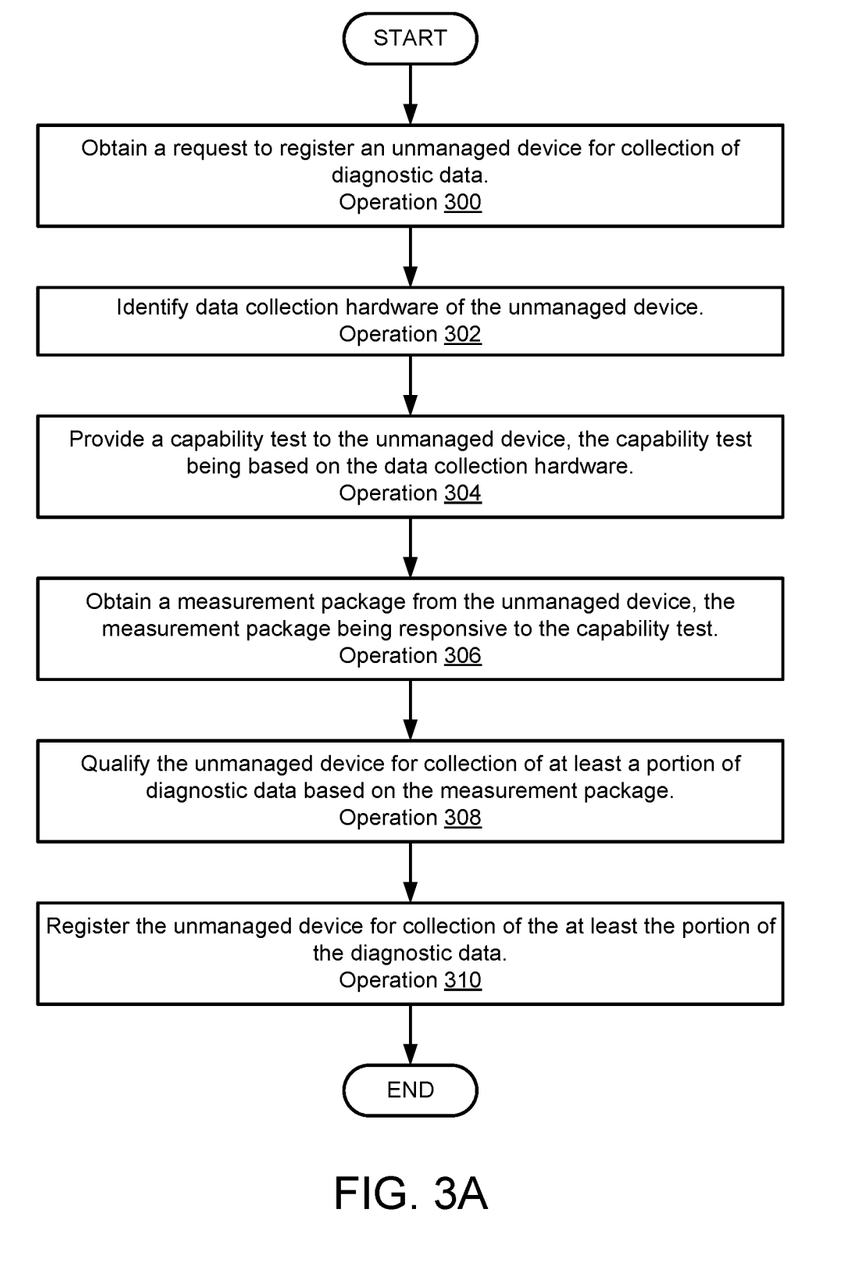
FIGS. 3A-3B show flow diagrams illustrating methods of managing data collection in accordance with an embodiment.
Figure 3B:
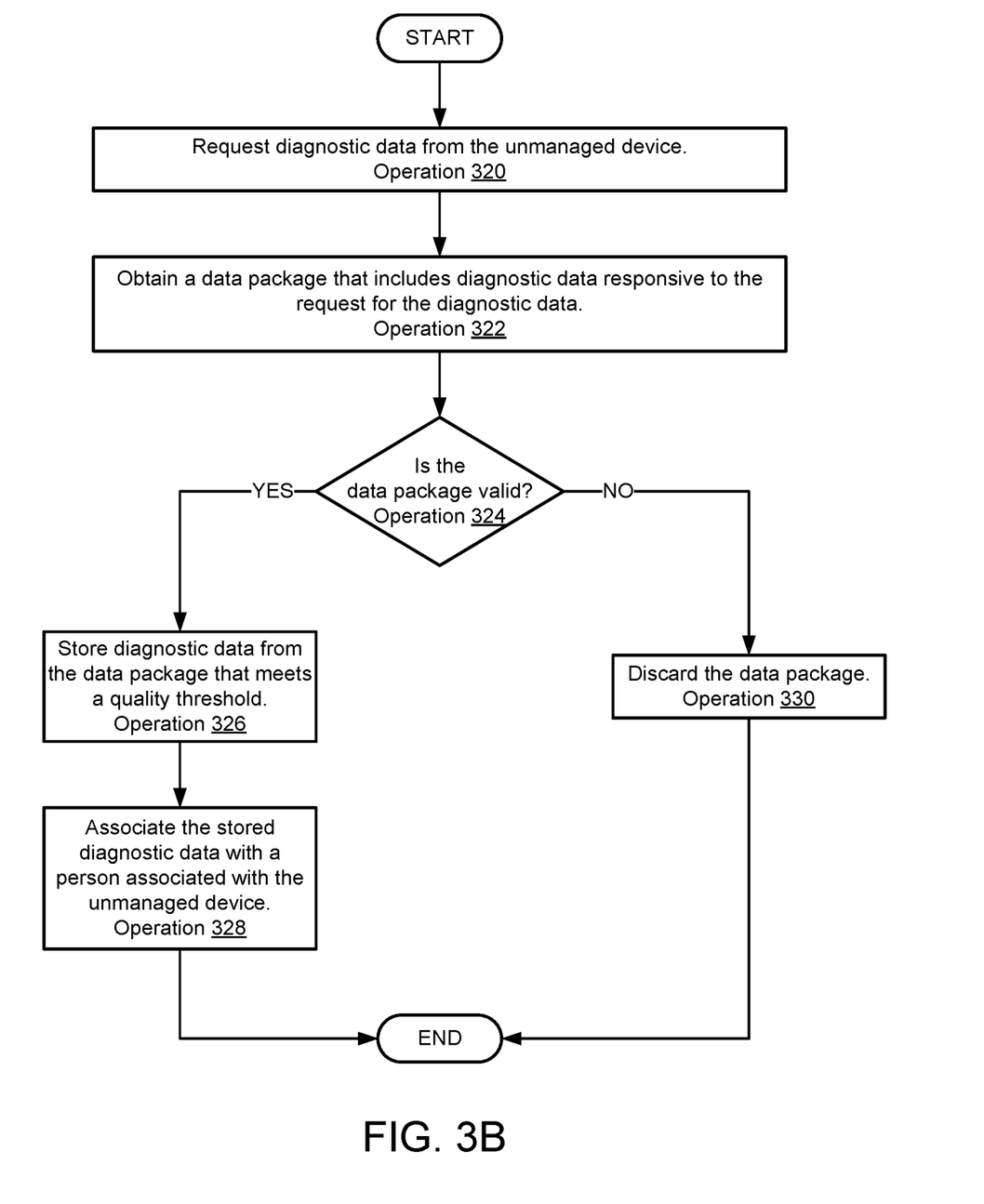

When providing their functionality, any of data collector 100 and data management system 106 may perform all, or a portion, of the methods illustrated in FIGS. 3A-3B.

Any of data collector 100 and data management system 106 may be implemented using a computing device (also referred to as a data processing system) such as a host or a server, a personal computer (e.g., desktops, laptops, and tablets), a "thin" client, a personal digital assistant (PDA), a Web enabled appliance, a mobile phone (e.g., Smartphone), an embedded system, local controllers, an edge node, and/or any other type of data processing device or system. For additional details regarding computing devices, refer to FIG. 4.

Data management system 106 may be implemented with multiple computing devices. For example, data management system 106 may be implemented with a data center, cloud installation, or other type of computing environment. The computing environment may host a software stack for registering data collectors, and system for obtaining and managing diagnostic information.

Any of the components illustrated in FIG. 1 may be operably connected to each other (and/or components not illustrated) with communication system 108. In an embodiment, communication system 108 includes one or more networks that facilitate communication between any number of components. The networks may include wired networks and/or wireless networks (e.g., and/or the Internet). The networks may operate in accordance with any number and types of communication protocols (e.g., such as the internet protocol).

While illustrated in FIG. 1 as including a limited number of specific components, a system in accordance with an embodiment may include fewer, additional, and/or different components than those illustrated therein.

Additionally, while illustrated in FIG. 1 with respect to a single data collector 100, it will be appreciated that the system may include any number of data collector 100 which may each collect similar and/or different diagnostic data. For example, a patient may have both a smart phone and smart watch. Each may include some similar sensors and some different sensors through which diagnostic information may be obtained and provided to data management system 106.

To further clarify embodiments disclosed herein, diagrams illustrating data flows implemented by and data structures used by a system over time in accordance with an embodiment are shown in FIGS. 2A-2B.

Turning to FIG. 2A, a first data flow diagram illustrating data flows, data processing, and/or other operations that may be performed by the system of FIG. 1 in accordance with an embodiment is shown.

To manage collection of data from data collector 100, data management system 106 may require that data collector 100 be registered with it prior to allowing diagnostic data to be obtained and used for diagnostic purposes. To register, data collector 100 may perform registration process 200. During registration process 200, data collector 100 may send a registration request to device registration process 250 performed by data management system 106.

The registration request may include information regarding data collector 100. For example, the registration request may include an inventory of hardware and software hosted by data collector 100, may include identifying information such as a part number, revision number, product identifier, and/or other types of information regarding data collector 100. Additionally, the registration request may include information regarding a person that will provide diagnostic data using data collector 100, or may not include information regarding the person (e.g., the information regarding the person may be provided to data management system 106 via other processes).

Once obtained, device registration process 250 may use the information to (i) establish a registration for data collector 100 in registration repository 252, (ii) generate cryptographic data usable to secure data provided by data collector 100, (iii) generate an identifier, stamp, and/or other metadata through which data collector 100 may identify itself, (iv) identifying tests for qualifying the capabilities of data collector 100, and/or (v) a provide registration package to data collector 100 which may include any of the aforementioned information (e.g., cryptographic data, identifier, test) and/or information based on the aforementioned information.

When obtained by registration process 200, the cryptographic data and/or identifier/stamp/other metadata may be stored as registration data 204 for future use. Additionally, qualification process 202 may be initiated. During qualification process 202, any number of tests (e.g., as specified in the registration package) on hardware components 210 of data collector 100 may be performed. The test may attempt to identify the extent to which hardware components 210 meet expectations (e.g., nominal operation).

The tests may attempt to identify, for example, (i) the dynamic range, sensitivity, and/or other characteristics of sensors (e.g., microphones, light sensors, charge coupled devices, etc.); (ii) the range, fidelity, and/or other characteristics of sources (e.g., speakers, light emission devices, etc.); (iii) interference between sources and sensors; etc.

The testing may be performed by causing various actions to be performed and measurements to be taken. The testing may involve a person. For example, during performance of a test a prompt may be provided to a person operating data collector 100. User feedback may also be obtained during the testing (e.g., a user may indicate that certain portions of a prompt are completed, in process of being completed, that certain conditions are currently met, etc.). The prompts and user feedback may be used during the testing to improve the likelihood that data collector 100 is in an expected condition during the testing.

The measurements obtained during the testing may be used to obtain a measurement package. The measurement package may include any type and quantity of information based on the measurements which may be used to gauge (i) how well operation of the hardware components 210 conforms to nominal operation, (ii) the extent of deviation of the operation of the hardware components 210 from nominal operation, etc.

The measurement package may include an identifier and may be encrypted using information included in registration data 204.

Once obtained by data management system 106, the measurement package may be used to update the information regarding data collector 100 included in registration repository 252. For example, registration repository 252 may be updated to (i) associate the capabilities and limitations specified by measurement package with the identifier/cryptographic information provided in registration package, (ii) specify additional information based on the information included in measurement package, such as data management system 106 imposed limits on the use of hardware components 210 due to undesired operation of hardware components 210 (e.g., significant deviation of operation from nominal operation), etc.

Once updated, the information in registration repository 252 may be usable to (i) ascertain to which person information obtained from data collector 100 should be associated, (ii) decrypt the data from data collector 100, (iii) screen portions of the data from future use (e.g., based on performance of hardware components 210 used to obtain the portions of the data), and/or (iv) annotate the obtain data with metadata usable to characterize the quality and/or other characteristics of the data obtained from data collector 100.

Turning to FIG. 2B, a second data flow diagram illustrating data flows, data processing, and/or other operations that may be performed by the system of FIG. 1 in accordance with an embodiment is shown.

After registration of data collector 100 is complete, data management system 106 may perform data ingest process 260 through which diagnostic information from data collector 100 may be ingested. To initiate ingestion of diagnostic information, a data request may be provided to data collector 100. The data request may drive data collection process 220. During data collection process 220, diagnostic data as specified by data request may be collected using hardware components 210. For example, various sensors, generative, and display components of data collector 100 may be operated to perform diagnostic data collection.

The display components may be used to display prompts to a user of data collector 100. The generative components may be used to generate various stimulations (e.g., optical, audio, etc.) of the user. The sensors may be used to obtain information regarding the user and the impact of the stimulations on the user. The sensed information and/or information regarding the generative processes may be collected.

In addition to the aforementioned sensing process to obtain diagnostic information, a characterization process may also be performed. The characterization process may be similar to qualification process 202. Through the characterization process, information regarding the operation of hardware components 210 may be collected.

The diagnostic information, information regarding the operation of hardware components 210, and/or other information may be added to a measurement package. The measurement package may be signed (or otherwise attested to by data collector 100), encrypted (e.g., using a keypair or other cryptographic data), and/or identifying information (e.g., stamps) may be added to obtain a signed measurement package. The signed measurement package may be provided to data management system 106.

Data ingest process 260 may receive and analyze the signed measurement package using registration data (e.g., association between the stamp/cryptographic data/the user) from registration repository 252. Data ingest process 260 may (i) verify that the signed measurement package is from a registered device, (ii) identify the person (e.g., patient) to which the included diagnostic data is to be associated, (iii) discriminate reliable from unreliable diagnostic information (e.g., based on the qualification process, described with respect to FIG. 2A), and (iv) store the reliable diagnostic information in data repository 262 (e.g., along with associations to the person, metrics regarding the quality of the diagnostic information, etc.).

In an embodiment, any of data collector 100 and data management system 106 are implemented using a hardware device including circuitry. The hardware device may be, for example, a digital signal processor, a field programmable gate array, or an application specific integrated circuit. The circuitry may be adapted to cause the hardware device to perform the functionality of data collector 100 and/or data management system 106 as discussed herein. Data collector 100 and/or data management system 106 may be implemented using other types of hardware devices without departing embodiment disclosed herein.

In an embodiment, any of data collector 100 and data management system 106 are implemented using a processor adapted to execute computing code stored on a persistent storage that when executed by the processor performs the functionality of data collector 100 and/or data management system 106 discussed throughout this application. The processor may be a hardware processor including circuitry such as, for example, a central processing unit, a processing core, or a microcontroller. The processor may be other types of hardware devices for processing information without departing embodiment disclosed herein.

In an embodiment, any of data collector 100 and/or data management system 106 include storage which may be implemented using physical devices that provide data storage services (e.g., storing data and providing copies of previously stored data). The devices that provide data storage services may include hardware devices and/or logical devices. For example, storage may include any quantity and/or combination of memory devices (i.e., volatile storage), long term storage devices (i.e., persistent storage), other types of hardware devices that may provide short term and/or long term data storage services, and/or logical storage devices (e.g., virtual persistent storage/virtual volatile storage).

For example, storage may include a memory device (e.g., a dual in line memory device) in which data is stored and from which copies of previously stored data are provided. In another example, storage may include a persistent storage device (e.g., a solid-state disk drive) in which data is stored and from which copies of previously stored data is provided. In a still further example, storage may include (i) a memory device (e.g., a dual in line memory device) in which data is stored and from which copies of previously stored data are provided and (ii) a persistent storage device that stores a copy of the data stored in the memory device (e.g., to provide a copy of the data in the event that power loss or other issues with the memory device that may impact its ability to maintain the copy of the data cause the memory device to lose the data).

Storage may also be implemented using logical storage. A logical storage (e.g., virtual disk) may be implemented using one or more physical storage devices whose storage resources (all, or a portion) are allocated for use using a software layer. Thus, a logical storage may include both physical storage devices and an entity executing on a processor or other hardware device that allocates the storage resources of the physical storage devices.

The storage may store any of the data structures discussed herein. Any of these data structures may be implemented using, for example, lists, tables databases, linked lists, unstructured data, and/or other types of data structures.

As discussed above, the components of FIG. 1 may perform various methods to manage operation of data processing systems. FIGS. 3A-3B illustrate methods that may be performed by the components of the system of FIG. 1. In the diagram discussed below and shown in FIGS. 3A-3B, any of the operations may be repeated, performed in different orders, and/or performed in parallel with or in a partially overlapping in time manner with other operations.

Turning to FIG. 3A, a flow diagram illustrating a method for managing data collection in accordance with an embodiment is shown. The method may be performed by any of data collector 100, data management system 106, and/or other components of the system shown in FIG. 1.

Prior to operation 300, a person may interact with a healthcare provider to obtain medical services. As part of that process, the person may be instructed to provide the healthcare provider with information collectible using a data collector managed by the person rather than the healthcare provider (e.g., the data collector may not be part of a healthcare provider information technology system). For example, the healthcare provider may instruct the person to use their cell phone to collect diagnostic information which the healthcare provider may use to treat the person.

To facilitate acquisition of the diagnostic information, the person may be instructed to register their data collector with a healthcare provider information technology system (e.g., a data management system). To do so, the person may initiate the registration process by sending a request to the healthcare provider information technology system (e.g., by visiting a portal or other network accessible resource). The person may send the request using the data collector or another data processing system.

At operation 300, a request to register an unmanaged device (e.g., the data collector managed by the person) for collection of diagnostic data (e.g., which may include or otherwise represent the diagnostic information) may be obtained. The request may be obtained by receiving the request via a communication. For example, a data management system or another entity may manage a portal (e.g., a website) through which request for registration of devices may be registered. The person may provide the request via the portal.

The request may include (i) information regarding the person, (ii) information regarding the hardware components of the unmanaged device, (iii) information regarding software components of the unmanaged device, (iv) identification information (e.g., serial number, part number, product number, manufacturer, etc.) for the unmanaged device, and/or (v) other types of information usable to establish a registration for the unmanaged device.

The unmanaged device may be any type of data processing system that is not managed by the healthcare provider information technology system. For example, the unmanaged device may be a cell phone, smart watch, etc.

At operation 302, data collection hardware of the unmanaged device may be identified. The data collection hardware may be identified (i) using information included in the request, (ii) by obtaining information regarding the unmanaged device from the manufacturer or other source, (iii) by performing a lookup or other type of parsing operation using a data structure that specifies data collection hardware for different types of devices, and/or via other methods.

At operation 304, a capability test may be provided to the unmanaged device. The capability test may be based on the data collection hardware (e.g., based on the hardware components and/or the software components such as firmware, drivers, etc. of the data collection hardware).

The capability test may be provided by (i) obtaining the capability test, and (ii) providing the capability test to the unmanaged device. The capability test may be obtained by (i) reading the capability test from storage (e.g., different capability test for different types of data collection hardware may be stored in a data structure), (ii) obtaining the capability test from another device, (iii) generating the capability test (e.g., sub-tests for different data collection hardware components may be stored in a data structure, and the capability test may be generated by aggregating sub-tests corresponding to the data collection hardware components identified in operation 302), and/or via other methods.

The capability test may specify any number of actions to be performed by the unmanaged device and through which a data package may be obtained. The actions may include (i) activation of generative components (e.g., light emitting device, auditory generation devices, etc.), (ii) activation of sensing components (e.g., microphones, charge coupled devices, etc.), (iii) prompts to be displayed, (iv) user input to be collected during performance of the capability test, etc.

At operation 306, a measurement package from the unmanaged device may be obtained. The measurement package may be responsive to the capability test. In other words, the measurement package may include data specified by the capability test.

The measurement package may be obtained by receiving the measurement package from the unmanaged device, or another device.

At operation 308, the unmanaged device may be qualified for collection of at least a portion of the diagnostic data based on the measurement package. The unmanaged device may by qualified by (i) identifying levels of divergence of the data collection hardware from nominal operation, (ii) comparing the levels of divergence to thresholds or other criteria, and (iii) establishing procedures for processing different types of diagnostic data obtained using the data collection hardware based on the comparisons.

For example, consider a scenario in which an unmanaged device includes a microphone as part of data collection hardware. The measurement package may specify a dynamic range for the microphone. The dynamic range may be compared to an expected dynamic range for the microphone during nominal operation of the microphone. A delta between the dynamic range and the expected dynamic range may be identified. The delta may be analyzed using criteria (e.g., thresholds). The criteria may specify progressively larger deltas. Each of the criteria may be associated with different procedures for processing diagnostic data obtained using the microphone.

The procedures may include (i) adding metadata to the diagnostic data that specifies the extent of deviation of the dynamic range from the expected dynamic range, (ii) portions of the diagnostic data that are to be discarded (e.g., diagnostic data that is too close to the dynamic range limits for the microphone, indicating that such diagnostic data is not reliable), (iii) discarding all diagnostic data collected using the microphone (e.g., in cases in which the dynamic range deviates to such a large degree that any collected data is likely to be unreliable), and/or other types of procedures. In this scenario, procedures (i)-(iii) may each be associated with criteria that requires progressively larger deviations between the dynamic range and expected dynamic range for the microphone. Thus, depending on the actual performance of the microphone, the procedures for processing diagnostic data collected using the microphone may vary.

The procedures may be established by recording the procedures in a data structure and associating the procedures with the corresponding data collection hardware components. Any number of processing procedures may be established for any quantity of data collection hardware.

At operation 310, the unmanaged device is registered for collection of the at least the portion of the diagnostic data. The unmanaged device may be registered by (i) providing the unmanaged device with an identifier to identify itself to a data management system, (ii) providing the unmanaged device with cryptographic data usable to secure transmission of diagnostic data, and/or other information usable to identify itself the data management system, secure diagnostic data, and/or otherwise facilitate collection of diagnostic data. Additionally, the unmanaged device may be register by storing similar information in a record managed by the data management system. The record may also include (i) identifying information for the unmanaged device, (ii) associations to corresponding procedures for processing diagnostic data from the unmanaged system, (iii) associations to persons for which the diagnostic data is collection, and/or other types of information usable to manage diagnostic data collection.

The method may end following operation 310.

After registration, diagnostic data may be collected from the unmanaged device.

Turning to FIG. 3B, a flow diagram illustrating a method of collecting diagnostic data from unmanaged devices in accordance with an embodiment is shown. The method may be performed by any of data collector 100, data management system 106, and/or other components of the system shown in FIG. 1.

Prior to operation 320, a data management system or another device may determine that diagnostic data for the patient may be desired for treatment purposes. A request for diagnostic data may be generated to obtain the diagnostic data.

At operation 320, a request for diagnostic data from an unmanaged device is obtained. The request for the diagnostic data may be obtained by (i) receiving the request from another device, (ii) generating the request (e.g., an application or other piece of software hosted by the unmanaged device may generate the request, or a data management system may generate the request), and/or via other methods. If the request is generated by a data management system, the request may be sent to the unmanaged device.

At operation 322, a data package that includes diagnostic data is obtained. The diagnostic data may be responsive to the request, or may be independent from the request. For example, a user of the unmanaged device may independently initiate collection of diagnostic data.

The data package may be obtained by receiving it from the unmanaged device, or another device.

At operation 324, a determination is made regarding whether the data package is valid. The determination may be made by (i) comparing identifying information (e.g., stamps) to corresponding information stored in records managed by a data management system for registered devices, and (ii) attempting to decrypt the data using cryptographic data established during registration of the unmanaged device. If the comparison indicates that the unmanaged device is not registered (e.g., no corresponding record) or that the data package cannot be decrypted, then it may be determined that the data package is not valid. If the comparison indicates that the unmanaged device is registered (e.g., no corresponding record) and that the data package can be decrypted, then it may be determined that the data package is valid.

If the data package is valid, then the method may proceed to operation 326. Otherwise the method may proceed to operation 330.

At operation 326, the diagnostic data from the data package that meets quality thresholds may be stored. The diagnostic data from the data package that meets quality thresholds may be stored by (i) identifying procedures for processing portions of the diagnostic data based on the data collection components used to obtain the respective portions, and (ii) implementing the procedures corresponding to the respective portions of the diagnostic data. In this manner, various portions may be (i) stored without modification, (ii) other portions may be stored with added metadata, (iii) various portions may be discarded without storing them, and (iv) all portions may be discarded if so specified by the procedures.

In the event that the data package also includes calibration data indicating the current capabilities of the data collection hardware of the unmanaged device when the diagnostic data was obtained, the calibration data may be used to at least temporarily update the procedures used to process the diagnostic data. For example, a similar qualification process as described with respect to operation 308 may be performed using the calibration data. The resulting procedures may be used to process the diagnostic data in the data package and/or may be used to update the procedures maintained by the data management system for the unmanage device.

At operation 328, the stored diagnostic data is associated with a person associated with the unmanaged device. The stored diagnostic data may be associated by (i) adding metadata reflecting the associations, (ii) updating table or other data structures that define how stored data is associated with persons, and/or via other methods.

The method may end following operation 328.

Returning to operation 324, the method may proceed to operation 330 if the data package is not valid.

At operation 330, the data package is discarded. The data package may be discarded by deleting the data package without storing information regarding the data package for future use.

Metadata indicating that the data package had been obtained and discarded may be stored for future use.

The method may end following operation 330.

Using the methods illustrated in FIGS. 3A-3B, embodiments disclosed here in may facilitate collection of diagnostic data from unmanaged devices while improving the likelihood that the collected diagnostic data is usable for diagnostic purposes. For example, the disclosed methods may reduce the likelihood of malicious entities interjecting falsified diagnostic data and improve the likelihood that limits on the quality of the collected diagnostic data are understood by users (e.g., healthcare providers) of the diagnostic data.

In contrast to managed devices which may undergo regular maintenance and performance testing, may generally be secured physically, and may otherwise be less likely to provide low quality or malicious information, unmanaged device may not be similarly managed. However, by virtue of these management procedures for managed devices, the managed devices may be less able to provide large amounts of diagnostic data over time for different persons (e.g., to logistic and cost requirements). These limits may reduce the likelihood of successfully diagnosing patient conditions by virtue of limited quantities of diagnostic data availability for persons. By facilitating supplementation of diagnostic data collection through unmanaged devices, embodiments disclosed herein may improve the likelihood of successful diagnosis and treatment through increased collection of diagnostic data.

Figure 4:
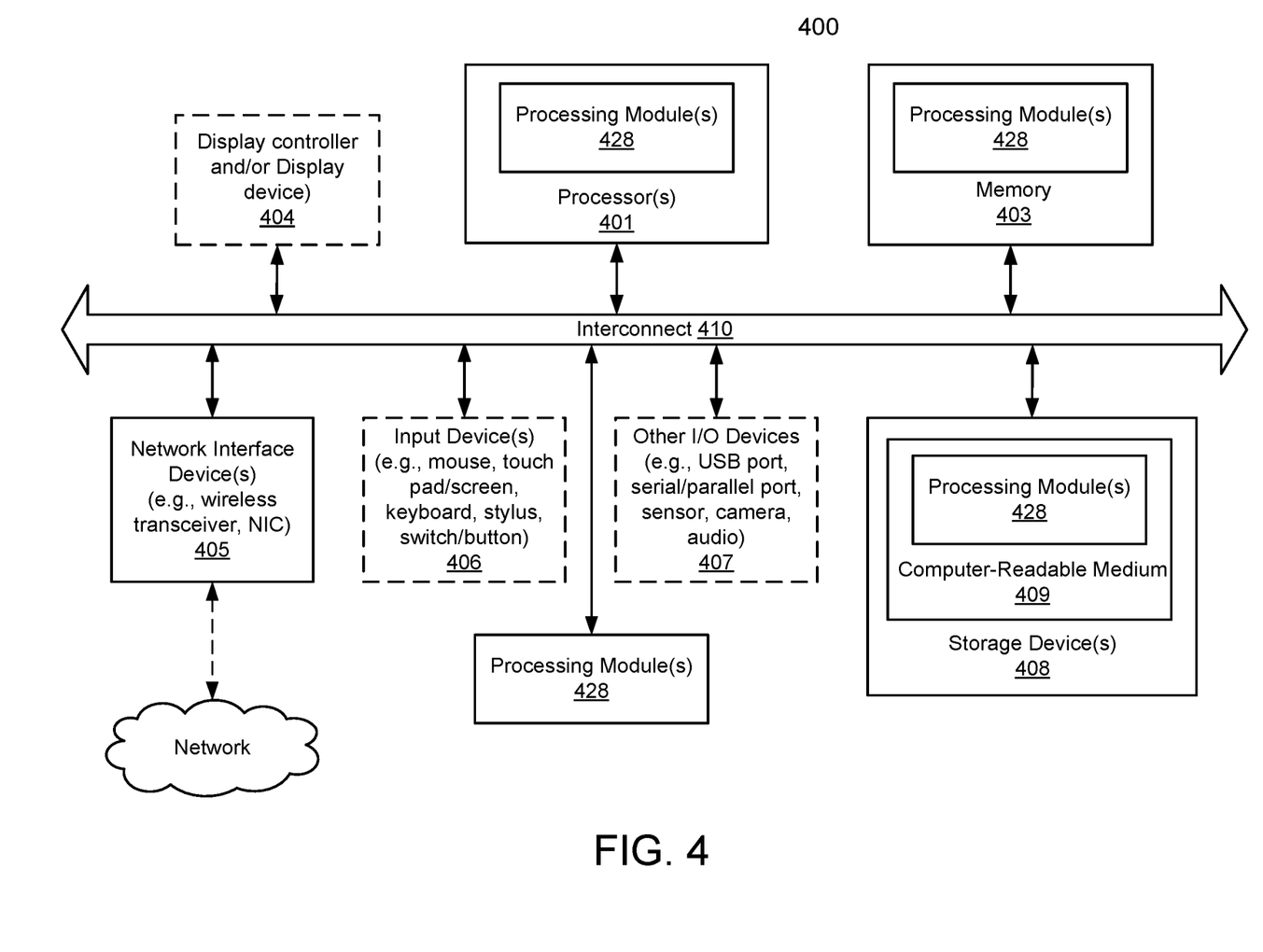
FIG. 4 shows a block diagram illustrating a data processing system in accordance with an embodiment.

Any of the components illustrated in FIGS. 1-2B may be implemented with one or more computing devices. Turning to FIG. 4, a block diagram illustrating an example of a data processing system (e.g., a computing device) in accordance with an embodiment is shown. For example, system 400 may represent any of data processing systems described above performing any of the processes or methods described above. System 400 can include many different components. These components can be implemented as integrated circuits (ICs), portions thereof, discrete electronic devices, or other modules adapted to a circuit board such as a motherboard or add-in card of the computer system, or as components otherwise incorporated within a chassis of the computer system. Note also that system 400 is intended to show a high level view of many components of the computer system. However, it is to be understood that additional components may be present in certain implementations and furthermore, different arrangement of the components shown may occur in other implementations. System 400 may represent a desktop, a laptop, a tablet, a server, a mobile phone, a media player, a personal digital assistant (PDA), a personal communicator, a gaming device, a network router or hub, a wireless access point (AP) or repeater, a set-top box, or a combination thereof. Further, while only a single machine or system is illustrated, the term "machine" or "system" shall also be taken to include any collection of machines or systems that individually or jointly execute a set (or multiple sets) of instructions to perform any one or more of the methodologies discussed herein.

In one embodiment, system 400 includes processor 401, memory 403, and devices 405-407 via a bus or an interconnect 410. Processor 401 may represent a single processor or multiple processors with a single processor core or multiple processor cores included therein. Processor 401 may represent one or more general-purpose processors such as a microprocessor, a central processing unit (CPU), or the like. More particularly, processor 401 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processor 401 may also be one or more special-purpose processors such as an application specific integrated circuit (ASIC), a cellular or baseband processor, a field programmable gate array (FPGA), a digital signal processor (DSP), a network processor, a graphics processor, a network processor, a communications processor, a cryptographic processor, a co-processor, an embedded processor, or any other type of logic capable of processing instructions.

Processor 401, which may be a low power multi-core processor socket such as an ultra-low voltage processor, may act as a main processing unit and central hub for communication with the various components of the system. Such processor can be implemented as a system on chip (SoC). Processor 401 is configured to execute instructions for performing the operations discussed herein. System 400 may further include a graphics interface that communicates with optional graphics subsystem 404, which may include a display controller, a graphics processor, and/or a display device.

Processor 401 may communicate with memory 403, which in one embodiment can be implemented via multiple memory devices to provide for a given amount of system memory. Memory 403 may include one or more volatile storage (or memory) devices such as random access memory (RAM), dynamic RAM (DRAM), synchronous DRAM (SDRAM), static RAM (SRAM), or other types of storage devices. Memory 403 may store information including sequences of instructions that are executed by processor 401, or any other device. For example, executable code and/or data of a variety of operating systems, device drivers, firmware (e.g., input output basic system or BIOS), and/or applications can be loaded in memory 403 and executed by processor 401. An operating system can be any kind of operating systems, such as, for example, Windows® operating system from Microsoft®, Mac OS®/iOS® from Apple, Android® from Google®, Linux®, Unix®, or other real-time or embedded operating systems such as VxWorks.

System 400 may further include IO devices such as devices (e.g., 405, 406, 407, 408) including network interface device(s) 405, optional input device(s) 406, and other optional IO device(s) 407. Network interface device(s) 405 may include a wireless transceiver and/or a network interface card (NIC). The wireless transceiver may be a WiFi transceiver, an infrared transceiver, a Bluetooth transceiver, a WiMax transceiver, a wireless cellular telephony transceiver, a satellite transceiver (e.g., a global positioning system (GPS) transceiver), or other radio frequency (RF) transceivers, or a combination thereof. The NIC may be an Ethernet card.

Input device(s) 406 may include a mouse, a touch pad, a touch sensitive screen (which may be integrated with a display device of optional graphics subsystem 404), a pointer device such as a stylus, and/or a keyboard (e.g., physical keyboard or a virtual keyboard displayed as part of a touch sensitive screen). For example, input device(s) 406 may include a touch screen controller coupled to a touch screen. The touch screen and touch screen controller can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen.

IO devices 407 may include an audio device. An audio device may include a speaker and/or a microphone to facilitate voice-enabled functions, such as voice recognition, voice replication, digital recording, and/or telephony functions. Other IO devices 407 may further include universal serial bus (USB) port(s), parallel port(s), serial port(s), a printer, a network interface, a bus bridge (e.g., a PCI-PCI bridge), sensor(s) (e.g., a motion sensor such as an accelerometer, gyroscope, a magnetometer, a light sensor, compass, a proximity sensor, etc.), or a combination thereof. IO device(s) 407 may further include an imaging processing subsystem (e.g., a camera), which may include an optical sensor, such as a charged coupled device (CCD) or a complementary metal-oxide semiconductor (CMOS) optical sensor, utilized to facilitate camera functions, such as recording photographs and video clips. Certain sensors may be coupled to interconnect 410 via a sensor hub (not shown), while other devices such as a keyboard or thermal sensor may be controlled by an embedded controller (not shown), dependent upon the specific configuration or design of system 400.

To provide for persistent storage of information such as data, applications, one or more operating systems and so forth, a mass storage (not shown) may also couple to processor 401. In various embodiments, to enable a thinner and lighter system design as well as to improve system responsiveness, this mass storage may be implemented via a solid state device (SSD). However, in other embodiments, the mass storage may primarily be implemented using a hard disk drive (HDD) with a smaller amount of SSD storage to act as a SSD cache to enable non-volatile storage of context state and other such information during power down events so that a fast power up can occur on re-initiation of system activities. Also a flash device may be coupled to processor 401, e.g., via a serial peripheral interface (SPI). This flash device may provide for non-volatile storage of system software, including a basic input/output software (BIOS) as well as other firmware of the system.

Storage device 408 may include computer-readable storage medium 409 (also known as a machine-readable storage medium or a computer-readable medium) on which is stored one or more sets of instructions or software (e.g., processing module, unit, and/or processing module/unit/logic 428) embodying any one or more of the methodologies or functions described herein. Processing module/unit/logic 428 may represent any of the components described above. Processing module/unit/logic 428 may also reside, completely or at least partially, within memory 403 and/or within processor 401 during execution thereof by system 400, memory 403 and processor 401 also constituting machine-accessible storage media. Processing module/unit/logic 428 may further be transmitted or received over a network via network interface device(s) 405.

Computer-readable storage medium 409 may also be used to store some software functionalities described above persistently. While computer-readable storage medium 409 is shown in an exemplary embodiment to be a single medium, the term "computer-readable storage medium" should be taken to include a single medium or multiple media (e.g., a centralized or distributed database, and/or associated caches and servers) that store the one or more sets of instructions. The terms "computer-readable storage medium" shall also be taken to include any medium that is capable of storing or encoding a set of instructions for execution by the machine and that cause the machine to perform any one or more of the methodologies of embodiments disclosed herein. The term "computer-readable storage medium" shall accordingly be taken to include, but not be limited to, solid-state memories, and optical and magnetic media, or any other non-transitory machine-readable medium. Processing module/unit/logic 428, components and other features described herein can be implemented as discrete hardware components or integrated in the functionality of hardware components such as ASICS, FPGAs, DSPs or similar devices. In addition, processing module/unit/logic 428 can be implemented as firmware or functional circuitry within hardware devices. Further, processing module/unit/logic 428 can be implemented in any combination hardware devices and software components.

Note that while system 400 is illustrated with various components of a data processing system, it is not intended to represent any particular architecture or manner of interconnecting the components; as such details are not germane to embodiments disclosed herein. It will also be appreciated that network computers, handheld computers, mobile phones, servers, and/or other data processing systems which have fewer components or perhaps more components may also be used with embodiments disclosed herein.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments disclosed herein also relate to an apparatus for performing the operations herein. Such a computer program is stored in a non-transitory computer readable medium. A non-transitory machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments disclosed herein are not described with reference to any particular programming language. It will be appreciated that a variety of programming languages may be used to implement the teachings of embodiments disclosed herein.

In the foregoing specification, embodiments have been described with reference to specific exemplary embodiments thereof. It will be evident that various modifications may be made thereto without departing from the broader spirit and scope of the embodiments disclosed herein as set forth in the following claims. The specification and drawings are, accordingly, to be regarded in an illustrative sense rather than a restrictive sense.

What is claimed is:

1. A method for managing data collection for managed devices and unmanaged devices, the method being performed by a data collection system that manages the managed devices and comprising:
   obtaining a request to register an unmanaged device of the unmanaged devices for collection of the data, wherein the managed devices being managed by a first entity and implements a first set of digital security control mechanisms defined by the first entity, the unmanaged device being managed by a second entity different from the first entity and implements, before and after being registered for the collection of the data, a second set of digital security control mechanisms that are at least in part different from the first set of digital security mechanisms, and the second set of digital security control mechanisms being defined by a third entity different from the second entity and the first entity;

based on the request to register the unmanaged device and before registering the unmanaged device for the collection of the data:

identifying one or more data collection hardware of the unmanaged device;

providing a capability test to the unmanaged device to cause the unmanaged device to operate at least one of the one or more data collection hardware to generate a piece of data specified in the capability test;

obtaining a measurement package from the unmanaged device, the measurement package being responsive to the capability test and comprising the piece of data generated by at least one of the one or more data collection hardware; and qualifying the unmanaged device for collection of at least a portion of diagnostic data based on the measurement package; and registering, in response to the qualifying of the unmanaged device, the unmanaged device for collection of the at least the portion of the diagnostic data and causing, as part of the registering, the unmanaged device to follow at least one of the first set of digital security control mechanisms that is not part of the second set of digital security mechanisms.

2. The method of claim 1, wherein registering the unmanaged device and causing the unmanaged device to follow the at least one of the first set of digital security control mechanisms that is not part of the second set of digital security mechanisms comprises:

assigning an identifier to the unmanaged device to be appended by the unmanaged device to all subsequent measurement packages sent by the unmanaged device to the data collection system;

providing the identifier to the unmanaged device; and associating the at least the portion of the diagnostic data with the identifier.

3. The method of claim 2, wherein the diagnostic data comprises data categories, and the at least the portion of the diagnostic data specifies a subset of the data categories.

4. The method of claim 3, further comprising:

after the registering of the unmanaged device is complete:

obtaining a second measurement package from the unmanaged device, the second measurement package being one of the subsequent measurement packages;

identifying a first portion of measurement data of the second measurement package, the first portion of the measurement data being a member of the subset of the data categories;

identifying a second portion of the measurement data of the second measurement package, the second portion of the measurement data not being a member of the subset of the data categories;

storing the first portion of the measurement data; and discarding the second portion of the measurement data.

5. The method of claim 4, wherein storing the first portion of the measurement data comprises:

extracting, from the second measurement package, a stamp based at least in part on the identifier;

identifying a user associated with the unmanaged device; and adding the first portion of the measurement data to a record associated with the user.

6. The method of claim 5, wherein adding the first portion of the measurement data comprises:

obtaining cryptographic data based on the user and a host of the record;

encrypting the first portion of the measurement data using the cryptographic data; and writing the encrypted first portion of the measurement data to storage for the record.

7. The method of claim 2, further comprising:

identifying software hosted by the unmanaged device, wherein the capability test is also based on the software hosted by the unmanaged device.

8. The method of claim 1, wherein the unmanaged device is a personal electronic device, and the managed devices are diagnostic equipment.

9. The method of claim 8, wherein the personal electronic device is a smart watch, a communication device, or a wearable sensing system.

10. The method of claim 8, wherein the managed devices are members of a healthcare provider information technology system, and the person electronic device is not a member of the healthcare provider information technology system.

11. A non-transitory machine-readable medium having instructions stored therein, which when executed by a processor cause operations for managing data collection for managed devices and unmanaged devices, the operations being performed by a data collection system that manages the managed device, the operations comprising:

obtaining a request to register an unmanaged device of the unmanaged devices for collection of the data, wherein the managed devices being managed by a first entity and implements a first set of digital security control mechanisms defined by the first entity, the unmanaged device being managed by a second entity different from the first entity and implements, before and after being registered for the collection of the data, a second set of digital security control mechanisms that are at least in part different from the first set of digital security mechanisms, and the second set of digital security control mechanisms being defined by a third entity different from the second entity and the first entity;

based on the request to register the unmanaged device and before registering the unmanaged device for the collection of the data:

identifying one or more data collection hardware of the unmanaged device;

providing a capability test to the unmanaged device to cause the unmanaged device to operate at least one of the one or more data collection hardware to generate a piece of data specified in the capability test;

obtaining a measurement package from the unmanaged device, the measurement package being responsive to the capability test and comprising the piece of data generated by at least one of the one or more data collection hardware; and qualifying the unmanaged device for collection of at least a portion of diagnostic data based on the measurement package; and

19 registering, in response to the qualifying of the unmanaged device, the unmanaged device for collection of the at least the portion of the diagnostic data and causing, as part of the registering, the unmanaged device to follow at least one of the first set of digital security control mechanisms that is not part of the second set of digital security mechanisms.

12. The non-transitory machine-readable medium of claim 11, wherein registering the unmanaged device and causing the unmanaged device to follow the at least one of the first set of digital security control mechanisms that is not part of the second set of digital security mechanisms comprises:
   assigning an identifier to the unmanaged device to be appended by the unmanaged device to all subsequent measurement packages sent by the unmanaged device to the data collection system;
   providing the identifier to the unmanaged device; and
   associating the at least the portion of the diagnostic data with the identifier.

13. The non-transitory machine-readable medium of claim 12, wherein the diagnostic data comprises data categories, and the at least the portion of the diagnostic data specifies a subset of the data categories.

14. The non-transitory machine-readable medium of claim 13, wherein the operations further comprise:
   after the registering of the unmanaged device is complete:
      obtaining a second measurement package from the unmanaged device, the second measurement package being one of the subsequent measurement packages;
      identifying a first portion of measurement data of the second measurement package, the first portion of the measurement data being a member of the subset of the data categories;
      identifying a second portion of the measurement data of the second measurement package, the second portion of the measurement data not being a member of the subset of the data categories;
      storing the first portion of the measurement data; and
      discarding the second portion of the measurement data.

15. The non-transitory machine-readable medium of claim 14, wherein storing the first portion of the measurement data comprises:
   extracting, from the second measurement package, a stamp based at least in part on the identifier;
   identifying a user associated with the unmanaged device; and
   adding the first portion of the measurement data to a record associated with the user.

16. A data processing system configured as a data collection system, comprising:
   a processor; and
   a memory coupled to the processor to store instructions, which when executed by the processor, cause the processor to perform operations for managing data collection for managed devices and unmanaged devices, the data collection system also manages the managed devices and the operations comprising:
      obtaining a request to register an unmanaged device of the unmanaged devices for collection of the data, wherein
         the managed devices being managed by a first entity and implements a first set of digital security control mechanisms defined by the first entity,
         the unmanaged device being managed by a second entity different from the first entity and implements, before and after being registered for the collection of the data, a second set of digital security control mechanisms that are at least in part different from the first set of digital security mechanisms, and
         the second set of digital security control mechanisms being defined by a third entity different from the second entity and the first entity;
      based on the request to register the unmanaged device and before registering the unmanaged device for the collection of the data:
         identifying one or more data collection hardware of the unmanaged device;
         providing a capability test to the unmanaged device to cause the unmanaged device to operate at least one of the one or more data collection hardware to generate a piece of data specified in the capability test;
         obtaining a measurement package from the unmanaged device, the measurement package being responsive to the capability test and comprising the piece of data generated by at least one of the one or more data collection hardware; and
         qualifying the unmanaged device for collection of at least a portion of diagnostic data based on the measurement package; and
      registering, in response to the qualifying of the unmanaged device, the unmanaged device for collection of the at least the portion of the diagnostic data and causing, as part of the registering, the unmanaged device to follow at least one of the first set of digital security control mechanisms that is not part of the second set of digital security mechanisms.

17. The data processing system of claim 16, wherein registering the unmanaged device and causing the unmanaged device to follow the at least one of the first set of digital security control mechanisms that is not part of the second set of digital security mechanisms comprises:
   assigning an identifier to the unmanaged device to be appended by the unmanaged device to all subsequent measurement packages sent by the unmanaged device to the data collection system;
   providing the identifier to the unmanaged device; and
   associating the at least the portion of the diagnostic data with the identifier.

18. The data processing system of claim 17, wherein the diagnostic data comprises data categories, and the at least the portion of the diagnostic data specifies a subset of the data categories.

19. The data processing system of claim 18, wherein the operations further comprise:
   after the registering of the unmanaged device is complete:
      obtaining a second measurement package from the unmanaged device, the second measurement package being one of the subsequent measurement packages;
      identifying a first portion of measurement data of the second measurement package, the first portion of the measurement data being a member of the subset of the data categories;
      identifying a second portion of the measurement data of the second measurement package, the second portion of the measurement data not being a member of the subset of the data categories;
      storing the first portion of the measurement data; and
      discarding the second portion of the measurement data.

20. The data processing system of claim 19, wherein storing the first portion of the measurement data comprises:
   extracting, from the second measurement package, a stamp based at least in part on the identifier;
   identifying a user associated with the unmanaged device; and
   adding the first portion of the measurement data to a record associated with the user.

* * * * *